(12) United States Patent
Moriyama et al.

(10) Patent No.: US 11,027,005 B2
(45) Date of Patent: Jun. 8, 2021

(54) METHOD FOR PRODUCING HIB CONJUGATE VACCINE USING PRP WITH LOWERED MOLECULAR WEIGHT

(71) Applicant: KM Biologies Co., Ltd., Kumamoto (JP)

(72) Inventors: Makoto Moriyama, Yamaga (JP); Katsuhiko Fukada, Koshi (JP); Kazuhiko Kimachi, Kumamoto (JP); Yuki Mihara, Kumamoto (JP); Hiroshi Yonemura, Kumamoto (JP); Yoichiro Kino, Kumamoto (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 0 days.

(21) Appl. No.: 16/340,778

(22) PCT Filed: Oct. 11, 2017

(86) PCT No.: PCT/JP2017/036781
§ 371 (c)(1),
(2) Date: Apr. 10, 2019

(87) PCT Pub. No.: WO2018/074296
PCT Pub. Date: Apr. 26, 2018

(65) Prior Publication Data
US 2020/0046822 A1 Feb. 13, 2020

(30) Foreign Application Priority Data
Oct. 20, 2016 (JP) .............................. JP2016-206033

(51) Int. Cl.
| A61K 39/385 | (2006.01) |
| A61K 39/102 | (2006.01) |
| A61P 31/16 | (2006.01) |
| A61K 39/00 | (2006.01) |

(52) U.S. Cl.
CPC .......... *A61K 39/102* (2013.01); *A61K 39/385* (2013.01); *A61P 31/16* (2018.01); *A61K 2039/6037* (2013.01)

(58) Field of Classification Search
CPC .................................................. A61K 39/102
See application file for complete search history.

(56) References Cited

U.S. PATENT DOCUMENTS

| 590,649 | A | 9/1897 | Ribyn, Jr. |
| 4,220,717 | A | 9/1980 | Kuo |
| 4,459,286 | A | 7/1984 | Hilleman et al. |
| 4,673,574 | A | 6/1987 | Anderson |
| 4,711,779 | A | 12/1987 | Porro et al. |
| 6,060,067 | A | 5/2000 | Sheppard et al. |
| 6,309,646 | B1 * | 10/2001 | Lees .................... A61K 39/385 |
| | | | 424/195.11 |
| 2007/0065460 | A1 | 3/2007 | Hamidi et al. |
| 2009/0010959 | A1 | 1/2009 | Biemans et al. |
| 2010/0158940 | A1 * | 6/2010 | Frings ..................... A61P 31/12 |
| | | | 424/201.1 |
| 2012/0107346 | A1 | 5/2012 | Contorni |
| 2012/0135125 | A1 * | 5/2012 | Muschiolik ............. A23L 33/21 |
| | | | 426/602 |
| 2015/0167036 | A1 | 6/2015 | Le Hir et al. |
| 2015/0328328 | A1 | 11/2015 | Han et al. |
| 2016/0015952 | A1 | 1/2016 | Omachi et al. |

FOREIGN PATENT DOCUMENTS

| EP | 0 161 188 | 5/1985 |
| EP | 0 208 375 | 7/1986 |
| EP | 0 477 508 | 8/1991 |
| JP | 62-30726 | 2/1987 |
| JP | 6-340550 | 12/1994 |
| JP | 7-509481 | 10/1995 |
| JP | 11-507026 | 6/1999 |
| JP | 2007-529503 | 10/2007 |
| JP | 2014-240395 | 12/2014 |
| JP | 2015-522272 | 8/2015 |
| JP | 2016-509081 | 3/2016 |
| WO | 93/15760 | 8/1993 |
| WO | 96/40242 | 12/1996 |
| WO | 2014/142135 | 9/2014 |
| WO | 2015/052684 | 4/2015 |

OTHER PUBLICATIONS

International Search Report dated Nov. 21, 2017 in International Appilcation No. PCT/JP2017/036781.
International Preliminary Report on Patentability dated May 2, 2019 in International Application No. PCT/JP2017/036781.
Milstien et al., "Global DTP manufacturing capacity and capability. Status report: Jan. 1995", Vaccine, vol. 14, No. 4, (1996) pp. 313-320.
Mawas et al., "Successful Induction of Protective Antibody Response against *Haemophilus influenzae* Type b and Diphtheria after Transcutaneous Immunization with the Glycoconjugate Polyribosyl Ribitol Phosphate—Cross-Reacting Material$_{197}$ Vaccine", The Journal of Infectious Diseases, 190, pp. 1177-1182, 2004.
Mawas et al., "Suppression and Modulation of Cellular and Humoral Immune Response to *Haemophilus influenzae* Type B (Hib) Conjugate Vaccine in Hib-Diphtheria-Tetanus Toxoids-Acellular Pertussis Combination Vaccines: A Study in a Rat Model", The Journal of Infectious Diseases, 191, pp. 58-64, 2005.

(Continued)

*Primary Examiner* — Albert M Navarro
(74) *Attorney, Agent, or Firm* — Wenderoth, Lind & Ponack, L.L.P.

(57) ABSTRACT

A method for preparing a PRP conjugate having high storage stability and a method for producing a Hib conjugate vaccine are provided. A method for preparing PRP conjugate in accordance with the embodiments of the present invention is characterized by that the release of PRPs after preparing the PRP conjugate is suppressed by using PRP with a lowered molecular weight than native PRP for a coupling reaction between PRP and a carrier protein. Also, a Hib conjugate vaccine comprising as an antigen the PRP conjugate prepared by said method has excellent storage stability and maintain sufficient immunogenicity.

12 Claims, 5 Drawing Sheets

(56) References Cited

OTHER PUBLICATIONS

Mawas et al., "Immune interaction between components of acellular pertussis-diphtheria-tetanus (DTaP) vaccine and *Haemophilus influenzae* b (Hib) conjugate vaccine in a rat model", Vaccine 24 (2006) pp. 3505-3512.

Fusco et al., "Preclinical studies on a recombinant group B meningococcal porin as a carrier for a novel *Haemophilus influenzae* type b conjugate vaccine", Vaccine 16, (1998), pp. 1842-1849.

Caufield et al., "Immunogenicity of a hexavalent combination vaccine in rhesus monkeys", Vaccine 19 (2001) pp. 902-907.

Cuervo et al., "Relationships among physico-chemical and biological tests for a synthetic Hib-TT conjugate vaccine", Vaccine 25 (2007) pp. 194-200.

Rana et al., "Development and characterization of *Haemophilus influenze* type b conjugate vaccine prepared using different polysaccharide chain lengths", Vaccine 33 (2015), pp. 2646-2654.

Chu et al., "Further Studies on the Immunogenicity of *Haemophilus influenzae* Type b and Pneumococcal Type b and Pneumococcal Type 6A Polysaccharide-Protein Conjugates", Infection and Immunity, vol. 40, No. 1, Apr. 1983, pp. 245-256.

Mawas et al., "Evaluation of the saccharide content and stability of the first WHO International Standard for *Haemophilus influenzae* b capsular polysaccharide", Biologicals 35 (2007), pp. 235-245.

Townsend et al., "Evaluation and validation of a serum bactericidal antibody assay for *Haemphilus influenzae* type b and the threshold of protection", Vaccine 32 (2014), pp. 5650-5656.

Lei et al., "Quantitation of low level unconjugated polysaccharide in tetanys toxoid-conjugate by HPAEC/PAD following rapid separation by deoxycholate/HCl", Journal of Pharmaceutical and Biomedical Analysis, 21 (6), (2000), pp. 1087-1091.

Tae Hyeon et al., "Measurement of Free Polysaccharide in Tetanus Toxoid-Conjugate Vaccine Using Antibody/Ammonium Sulfate Precipitation", Journal of Microbiology and Biotechnology (2003), 13 (3), pp. 469-472.

Extended European Search Report dated May 26, 2020 in corresponding European Patent Application No. 17863266.7.

Saydam et al., "Immunogenicity and thermal stability of a combined vaccine against *Haemophilus influenzae* type b and *Neisseria meningitidis* serogroup C Diseases", Vaccine, 2010, vol. 28, No. 38, pp. 6228-6234.

Tsai et al, "Quantification of polysaccharide in *Haemophilus influenzae* type b conjugate and polysaccharide vaccines by high-performance anion-exchange chromatography with pulsed amperometric detection", Vaccine, 1994, vol. 12, No. 8, pp. 700-706.

* cited by examiner

METHOD FOR PRODUCING HIB CONJUGATE VACCINE USING PRP WITH LOWERED MOLECULAR WEIGHT

TECHNICAL FIELD

The present invention relates to a method for preparing a polyribosylribitol phosphate (PRP) conjugate via a coupling reaction of PRP and a carrier protein and a method for producing a *Haemophilus influenzae* type b (Hib) conjugate vaccine.

BACKGROUND ART

*Haemophilus influenzae*, a Gram-negative coccobacillus facultative anaerobe, has "polymorphic character" as forming filamentary or coccoid forms and has no spore and flagella. It is classified into non-capsulated and capsulated strains based on the presence and absence of capsule. It is known that type b strain (Hib), which is a capsulated strain, has especially high pathogenicity. Hib infection is a major cause of meningitis of infants. Hib bacteria colonized at the upper respiratory tract invade into blood and spread to a whole body through bacteremia to cause systemic infection such as meningitis, epiglottitis, arthritis, and the like.

For the prevention of Hib infection, it is known that an antibody against capsular polysaccharide of Hib, PRP, is effective. However, a Hib vaccine of PRP component alone is non-dependent upon T cells and thus is not sufficiently effective for infants less than 18 months who have immature immune system. For this reason, a conjugate vaccine in which a carrier protein is conjugated to PRP to render the vaccine T cell dependent has been developed and used for infants.

A conjugate vaccine in which polysaccharide such as PRP is conjugated with a carrier protein is known. Patent reference 1 discloses a method for producing conjugate of Hib and a glycoprotein and the use of said conjugate. Patent reference 2 discloses an improved method for producing an oligosaccharide conjugate vaccine.

A method for producing PRP is also known. Patent reference 3 discloses a method comprising, after culturing Hib strain in a culture medium, purifying supernatant and extracting PRP.

Tetanus toxoid is required by WHO standard to have a purity of more than 1,000 Lf/mg PN. There is a report that 31 among 34 manufacturing companies around the world met the standard and 15 companies attained a purity of more than 1,500 LF/mg PN (Non-patent Reference 1). European Pharmacopoeia (EP) shows Hib conjugate vaccine standard as >1,500 Lf/mg PN. For the purification of tetanus toxoid, ammonium sulfate precipitation, trichloroacetic acid precipitation, column chromatography (gel filtration chromatography, affinity chromatography), salting-out, dialysis, and the like have been used.

Investigation on a conjugation ratio of a polysaccharide and a carrier protein is reported in Patent reference 4. According to Patent reference 4, a combined vaccine characterized by that a ratio of a polysaccharide to a protein is from 1:0.3 to 1:2 is disclosed.

As a method for evaluating immunogenicity of a Hib conjugate vaccine, an immunogenicity test using rats is known and an antibody titer is evaluated by ELISA (Enzyme-Linked Immunosorbent Assay; enzyme immunoassay) etc. (Non-patent references 2 to 4). Besides, immunogenicity tests using mice or guinea pig (Non-patent reference 5) or using monkey (Non-patent reference 6) are known.

It is known that free PRPs released from a PRP conjugate and an antibody to PRP are inversely related to each other and that a vaccine less likely to have increased free PRPs is important in view of stability and effectiveness (Non-patent reference 7).

It is reported in Non-patent reference 8 that a Hib conjugate was prepared by reductive amination using PRPs with different sizes and immunogenicity was evaluated.

PRIOR ART

Patent Reference

Patent reference 1: JP 62-30726
Patent reference 2: JP 6-340550
Patent reference 3: JP 2015-522272
Patent reference 4: JP 11-507026
Patent reference 5: PCT publication 93/15760
Patent reference 6: U.S. Pat. No. 4,673,574
Patent reference 7: EP 161188
Patent reference 8: EP 208375
Patent reference 9: EP 477508
Patent reference 10: U.S. Pat. No. 4,220,717
Patent reference 11: U.S. Pat. No. 4,459,286

Non-Patent Reference

Non-patent reference 1: Vaccine 14 (4) (1996) 313-320
Non-patent reference 2: The Journal of Infectious Diseases, 190, 1177-1182, 2004
Non-patent reference 3: The Journal of Infectious Diseases, 191, 58-64, 2005
Non-patent reference 4: Vaccine 24 (2006) 3505-3512
Non-patent reference 5: Vaccine 16 (1998) 1842-1849
Non-patent reference 6: Vaccine 19 (2001) 902-907
Non-patent reference 7: Vaccine 25 (2007) 194-200
Non-patent reference 8: Vaccine 33 (2015) 2646-2654
Non-patent reference 9: Infection and Immunity, 40 (1) 1983, 245-256
Non-patent reference 10: Biologicals 35 (2007) 235-245
Non-patent reference 11: Vaccine 32 (2014) 5650-5656
Non-patent reference 12: Vaccine 12 (8) (1994) 700-706
Non-patent reference 13: Journal of Pharmaceutical and Biomedical Analysis 21 (6) (2000) 1087-1091
Non-patent reference 14: Journal of Microbiology and Biotechnology (2003), 13(3), 469-472

DISCLOSURE OF THE INVENTION

Technical Problem to be Solved by the Invention

A Hib conjugate vaccine comprising PRP conjugate as an antigen exerts high immunogenicity and effective for infants. However, there is a problem of lowered storage stability due to PRP release from a carrier protein during storage of a vaccine. Although development of a more stable Hib conjugate vaccine is desired, an effective method for suppressing the increase in a content of released PRPs has not yet been reported.

The present invention is done in view of the above circumstances and provides a method for preparing a PRP conjugate having high storage stability and a method for producing a Hib conjugate vaccine.

Means for Solving the Problems

The present inventors have earnestly studied so as to solve the above problems. As a result, the present inventors have found a method for preparing a stable PRP conjugate with the increase in a content of released PRPs being suppressed by using PRP, a molecular weight of which is suitably lowered as compared to native PRP. Also, the present inventors have found a method for producing a Hib conjugate vaccine by earnestly investigating a weight ratio of PRP and a carrier protein when subjected to a reaction, a purity of a carrier protein (especially tetanus toxoid), and pH of a storage solution after preparing a PRP conjugate.

Thus, the present invention includes the followings.

[1] A method for preparing a polyribosylribitol phosphate (PRP) conjugate via a coupling reaction of PRP and a carrier protein wherein the method is characterized by that the release of PRPs after preparing the PRP conjugate is suppressed by using PRP with a lowered molecular weight than native PRP.

[2] The method of [1] wherein the PRP conjugate is stored in a solution of pH 5.4 to 6.3 after preparation of the PRP conjugate.

[3] The method of [2] wherein a released amount of PRPs in a stress test in a solution at pH 5.4 to 6.3 at 37° C. for 4 weeks is less than 50%.

[4] The method of any one of [1] to [3] wherein PRP with a lowered molecular weight is obtained by physical fracture.

[5] The method of any one of [1] to [3] wherein PRP with a lowered molecular weight is obtained by hydrolysis with an acid or an alkali.

[6] The method of any one of [1] to [5] wherein PRP with a lowered molecular weight has a molecular weight of 80 to 150 kDa.

[7] The method of any one of [1] to [6] wherein PRP and the carrier protein is subject to the coupling reaction for preparing the PRP conjugate at a weight ratio of from 2:1 to 4:1.

[8] The method of [7] wherein PRP and the carrier protein are subject to the coupling reaction at a weight ratio of 4:1.

[9] The method of any one of [1] to [8] wherein the method comprises a step of activating PRP with a lowered molecular weight using 1-cyano-4-(dimethylamino) pyridinium tetrafluoroborate (CDAP) before the coupling reaction for preparing the PRP conjugate.

[10] The method of any one of [1] to [9] wherein the carrier protein is tetanus toxoid.

[11] The method of [10] wherein a purity of tetanus toxoid is 2,500 to 3,500 LF/mg PN.

[12] The method of [11] wherein a purity of tetanus toxoid is 2,900 to 3,300 LF/mg PN.

[13] A method for producing a *Haemophilus influenzae* type b (Hib) conjugate vaccine comprising the method as set forth in any one of [1] to [11].

[14] Use of a Hib conjugate vaccine produced by the method of [13] as a combined vaccine.

[15] Use of a Hib conjugate vaccine produced by the method of [13] as a five combined vaccine with acellular pertussis/diphtheria/tetanus/inactivated polio vaccine.

Effects of the Invention

In accordance with the present invention, it becomes possible to store stably PRP conjugate after its preparation for a long period of time. Furthermore, it becomes possible to store stably a Hib conjugate vaccine with sufficient immunogenicity being maintained.

BRIEF DESCRIPTION OF DRAWINGS

Hereinbelow.

FIG. 1 is a graph showing a relationship between the increase in a content of free PRPs (%) and a molecular weight of PRP when PRP conjugate prepared by one embodiment of the present invention is stored at 37° C. for 4 weeks.

FIG. 2 is a graph showing immunogenicity of Hib conjugate vaccines comprising as an antigen PRP conjugates with a varied molecular weight prepared by one embodiment of the present invention when rats are immunized with 1/25 SHD (Single Human Dose) and 1/50 SHD of the vaccine.

FIG. 3 is a graph showing immunogenicity of Hib conjugate vaccines comprising as an antigen PRP conjugates prepared by one embodiment of the present invention with a varied weight ratio of PRP and a carrier protein to be subject to a coupling reaction when rats are immunized with 1/25 SHD and 1/50 SHD of the vaccine.

FIG. 4 is a graph showing immunogenicity of Hib conjugate combined vaccines comprising as an antigen PRP conjugates prepared by one embodiment of the present invention with a varied weight ratio of PRP and a carrier protein to be subject to a coupling reaction when rats are immunized with 1/100 SHD and 1/500 SHD of the vaccine.

FIG. 5 is a graph showing immunogenicity of Hib conjugate combined vaccines comprising as an antigen PRP conjugates prepared by one embodiment of the present invention when rats are immunized three times with a varied dose of the vaccine.

FIG. 6 is a graph showing a relationship between the increase in a content of free PRPs (%) and pH of a storage solution when Hib conjugate combined vaccines comprising as an antigen PRP conjugates prepared by one embodiment of the present invention with a varied weight ratio of PRP and a carrier protein to be subject to a coupling reaction is stored at 37° C. for 4 weeks.

FIG. 7 is a graph showing a relationship between the increase in a content of free PRPs (%) and pH of a storage solution when Hib conjugate combined vaccines comprising as an antigen PRP conjugates prepared by one embodiment of the present invention with a varied weight ratio of PRP and a carrier protein to be subject to a coupling reaction is stored at 10° C. for 45 months.

BEST MODE FOR CARRYING OUT THE INVENTION

Figure 1:
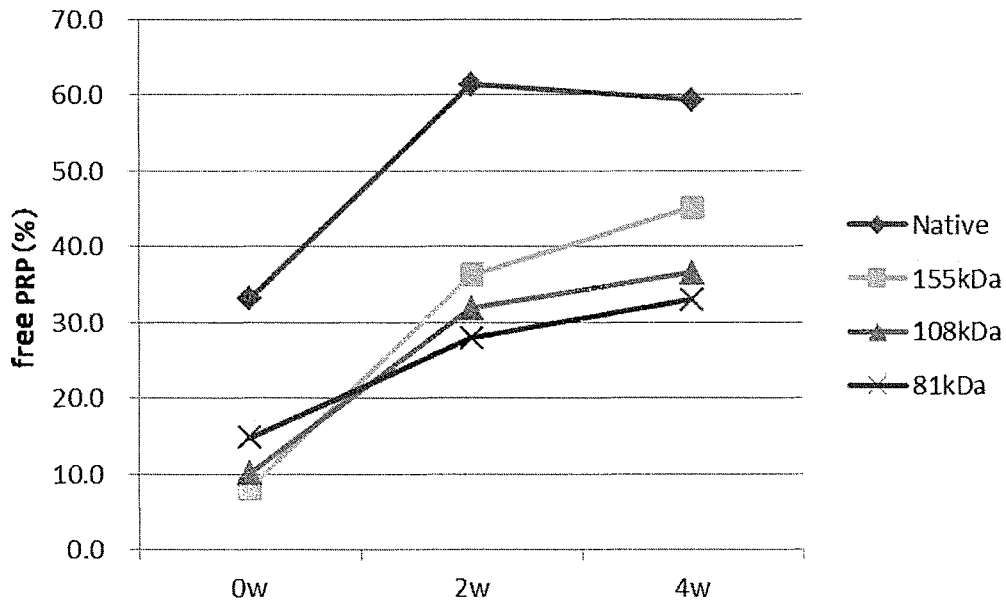
FIGS. 1 to 7 are explained.

In the following, preferable embodiments of the present invention are explained in detail. It should be noted that the present invention is not limited to the following embodiments.

A method for preparing PRP conjugate in accordance with the embodiments of the present invention is characterized by that the release of PRPs after preparing the PRP conjugate is suppressed by using PRP with a lowered molecular weight than native PRP for a coupling reaction between PRP and a carrier protein. Also, a Hib conjugate vaccine comprising as an antigen the PRP conjugate prepared by said method has excellent storage stability and maintain sufficient immunogenicity.

PRP conjugate may be prepared using known coupling techniques. For instance, PRP may be coupled via thioether linkage. In this coupling technique, PRP is activated with 1-cyano-4-(dimethylamino) pyridinium tetrafluoroborate (CDAP) to form a cyanate ester. The thus activated PRP may be bound to an amino group of a carrier protein directly or via a spacer group. Preferably, cyanate ester is bound to hexane diamine and hetero ligation accompanied by the formation of thioether is conducted to conjugate an amino-derivatized polysaccharide and a carrier protein (Patent reference 5).

In addition to the above, conjugate may also be prepared by reductive amination (Patent references 6 to 9). A still another method includes coupling cyanogen bromide (CNBr)-activated polysaccharide derivatized with adipic acid dihydrazide (ADH) to a carrier protein by carbodiimide condensation (Non-patent reference 9).

A carrier protein includes tetanus toxoid, pertussis toxoid, diphtheria toxoid, a genetic variant of diphtheria toxoid CRM197, non-capsulated *Haemophilus influenzae* D antigen, outer membrane protein (OMP) of *Neisseria meningitidis* group B, and the like. A typical carrier protein for PRP conjugate is tetanus toxoid.

In case that tetanus toxoid is used as a carrier protein, it is used at a purity of more than 1,000 Lf/mg PN in accordance with WHO standard. For the method of the present invention, tetanus toxoid is preferably used at as high a purity as possible and preferably at 2,500 to 3,500 Lf/mg PN, more preferably at 2,900 to 3,300 Lf/mg PN.

A method for preparing PRP with a lowered molecular weight includes physical fracture with a high-pressure emulsifier. In this case, fracture is done at a pressure of 10,000 to 30,000 psi for 10 minutes to 2 hours, preferably at a pressure of 20,000 to 30,000 psi for 10 minutes to 2 hours, more preferably at a pressure of 25,000 to 30,000 psi for 10 minutes to 2 hours.

A method for preparing PRP with a lowered molecular weight may also be done with hydrolysis using an acid, an acidifying agent or an alkali. An acid and an acidifying agent includes chloric acid, sulfuric acid, sodium periodate, and the like. An alkali includes sodium hydroxide, sodium hydrogen carbonate, and the like.

Native PRP, a molecular weight of which has not yet been lowered, has a molecular weight of around 250 to 400 kDa, and therefore PRP with a lowered molecular weight has a molecular weight of less than 250 kDa. In accordance with the present invention, it is preferably 80 to 150 kDa, more preferably 80 to 100 kDa.

Measurement of a molecular weight is performed using HPLC (High Performance Liquid Chromatography) apparatus as described in Non-patent references 10 and 11. In this case, a calibration curve is prepared using pullulan etc. and a molecular weight of peak top may be obtained as an equivalent of pullulan etc. Alternatively, an absolute molecular weight may be obtained using MALS (Multi Angle Light Scattering). Any other method may be used as far as it allows for measurement of a molecular weight.

An action mechanism that storage stability of PRP conjugate improves by using PRP with a lowered molecular weight is thought to be the following two: (1) in case of conjugate of PRP with a lowered molecular weight, the length of PRP bound to a carrier protein is short and thus, even if PRP is cut off by hydrolysis, a total amount of released PRPs decreases; (2) due to a lowered molecular weight of PRP, PRP present between conjugate is less likely to be cleaved, provided that, due to constraint in view of steric structure, a too much lowered molecular weight would not improve stability and therefore it is not that the shorter a size of PRP becomes the better.

In one embodiment of the present invention, in order to avoid excess antibody reaction against a carrier protein, and also to enhance vaccine productivity per a carrier protein by reducing its amount, PRP and a carrier protein are subject to a coupling reaction at a weight ratio ranging from 2:1 to 4:1. A weight ratio is more preferably 4:1.

pH of a storage solution of PRP conjugate is preferably 5.0 to 6.6, more preferably 5.4 to 6.3. For adjustment of pH, an acid such as chloric acid and acetic acid or an alkali solution such as sodium hydroxide and sodium hydrogen carbonate may be used or a buffer solution may also be used. For a storage solution, phosphate buffer, acetate buffer, or MES buffer may be used if composition that pH may be maintained in the above range. Other buffers such as succinate buffer may also be used.

Measurement of a content of free PRPs may be carried out by the methods disclosed in Non-patent references 12 to 14. Temperature conditions under which a long-term storage test is performed for investigating stability is 5±3° C. or less than 10° C. while avoiding freezing. Alternatively, evaluation may be done in an accelerated manner under higher temperature conditions.

Immunogenicity of a Hib conjugate vaccine prepared by the method according to the present invention may be obtained by immunizing an animal such as rat and monkey and measuring an anti-PRP antibody titer. An antibody titer may be measured by ELISA and the like. Alternatively, it may also be evaluated by Serum Bactericidal antibody (SBA) test using a complement and Hib bacteria as described in Non-patent reference 11. Since it is known that an antibody titer and SBA value are correlated to some extent as described in Non-patent reference 11, evaluation may also be done with an antibody titer by ELISA.

A Hib conjugate vaccine prepared by the method according to the present invention is less likely to cause immune interference and therefore may be used as a combined vaccine with another antigen, including, for instance, a combined vaccine with acellular pertussis/diphtheria/tetanus/inactivated polio vaccine etc.

A Hib conjugate vaccine prepared by the method according to the present invention may also be used with an adjuvant. A dosage form may be a liquid formulation or a lyophilized formulation.

The present invention is explained in more detail with the following examples but is not limited thereto.

Example 1

Production of PRPs with Lowered Molecular Weight

In accordance with the standard procedure as described in Patent references 10 and 11, Hib bacteria were cultured in BHI (Brain Heart Broth) medium supplemented with NAD (Nicotinamide Adenine Dinucleotide) at 37° C. for 8 to 14 hours and supernatant was purified by ethanol precipitation to give purified PRPs having a peak-top molecular weight of 250 to 400 kDa with calculated as pullulan. A process solution containing purified PRPs was treated 15 to 20 times at each pressure of 10,000 psi, 20,000 psi, or 30,000 psi with a high-pressure emulsifier (manufactured by Microfluidics) so as to physically fracture PRPs to give PRPs with a lowered molecular weight. The obtained PRPs with a lowered molecular weight were analyzed for their molecular size to confirm that they have a peak-top molecular weight of 155 kDa, 108 kDa and 81 kDa.

Example 2

Preparation of PRP Conjugate

The obtained PRPs with a lowered molecular weight were reacted at 2 to 12 mg/mL with CDAP at a concentration of 100 mg/mL under the condition that a weight ratio of CDAP to PRP is 0.2 to 2.0 and were further reacted with 0.5M ADH for 2 hours. Thereafter, dialysis was conducted to remove unreacted material to give activated PRPs, which were reacted with a tetanus toxoid (TT) drug substance (manufactured by The Chemo-Sero-Therapeutic Research Institute) at a purity of 2,900 to 3,300 LF/mg PN at a weight ratio of 1:1, 2:1 or 4:1 together with a condensing agent, EDC (1-ethyl-3-(3-dimethylaminopropyl)carbodiimide). Depending on the concentration, the reaction was performed for 40 minutes to 4 hours and then the reactant was dialyzed to give PRP conjugates having a PRP/TT ratio of 0.48, 0.77, and 1.0.

Example 3

Evaluation of Storage Stability of PRP Conjugates

Storage stability of the PRP conjugates as prepared (phosphate buffer solution, pH 6.8) was evaluated by a stress test at 37° C. After 2 weeks and 4 weeks of initiation of storage, a content of free PRPs (%) was measured using a ribose test described in Non-patent reference 10 after treatment with DOC as described in Non-patent reference 13. The results are shown in FIG. 1. It was found that, as compared to native PRP, a molecular weight of which is not lowered, and PRP of 155 kDa, PRPs with a lowered molecular weight such as 108 kDa and 81 kDa could suppress the increase in a content of free PRPs.

Example 4

Investigation of Effect of pH of PRP Conjugate Storage Solution

Phosphate buffers of pH 6.0, 6.3, 6.6, or 7.0 were prepared and the effect of pH of storage solution of PRP conjugate (a molecular weight of PRP after molecular weight lowering: 142 kDa) was evaluated under stress condition at 37° C. A content of free PRPs (%) at initiation of storage and after 2 weeks and 4 weeks was measured as described in Example 3. As a result, it was found that, within a range of pH 6 to 7, the lower pH becomes, the more the increase in a content of free PRPs (%) is suppressed (Table 1).

TABLE 1

| | | | Free PRPs (%) | | | | |
|---|---|---|---|---|---|---|---|
| Sample | PB | pH | 37° C., 0 w | 37° C., 2 w | 37° C., 4 w | Increased amount (2 w − 0 w) | 4 w − 0 w |
| Hib-TT | — | 7.0 | 5.71 | 30.9 | 34.8 | 25.2 | 29.1 |
| (PRP | 50 mmol/L | 6.6 | 3.08 | 17.2 | 25.7 | 14.1 | 22.6 |
| 142 | | 6.3 | 3.72 | 13.7 | 20.4 | 10.0 | 16.7 |
| kDa, | | 6.0 | 2.92 | 11.9 | 17.2 | 9.0 | 14.3 |
| 1:1) | 20 mmol/L | 6.6 | 3.77 | 16.3 | 23.8 | 12.5 | 20.0 |
| | | 6.3 | 3.40 | 11.9 | 18.7 | 8.5 | 15.3 |
| | | 6.0 | 3.50 | 10.2 | 15.4 | 6.7 | 11.9 |

Example 5

Evaluation of Immunogenicity of Hib Conjugate Vaccine

Figure 2:
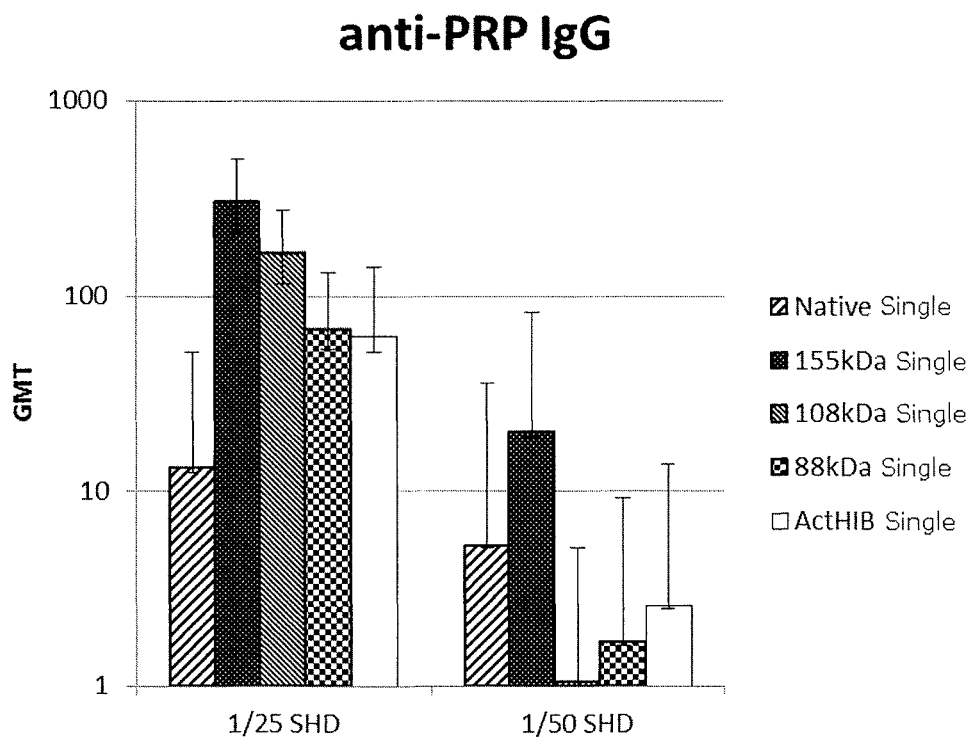
Figure 3:
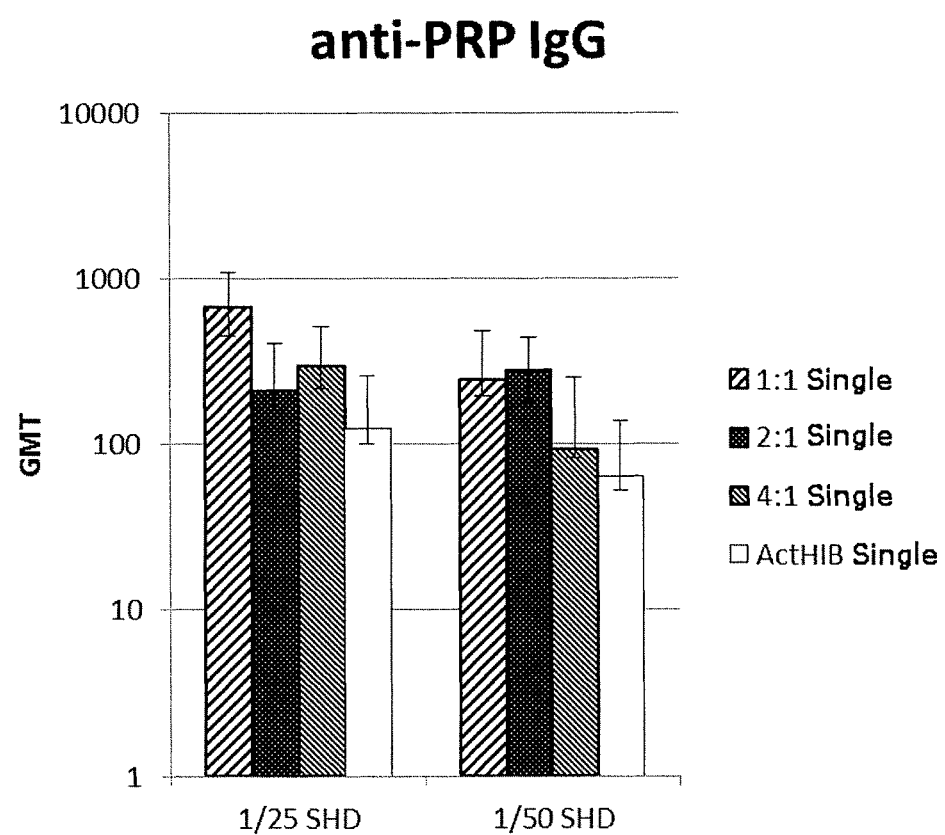

SD rats (female, 5 weeks old; each group consists of 5 animals) were subcutaneously inoculated at the back with 0.5 mL of Hib conjugate vaccine comprising as an antigen PRP conjugate (molecular weight of PRP: changing molecular weights such as Native, 155 kDa, 108 kDa, and 88 kDa, or with changing weight ratio of PRP and a carrier protein as prepared in Example 2). After four weeks, a second inoculation was performed. Two weeks after the second inoculation, blood was sampled and an antibody titer was measured with self-prepared ELISA. The results are shown in FIGS. 2 and 3. It was confirmed that anti-PRP antibody titer equivalent to or more than that of the known Hib conjugate vaccine (ActHIB (trade-name) manufactured by Sanofi Pasteur) was obtained.

Example 6

Preparation of Combined Vaccine Comprising PRP Conjugate and Evaluation of Immunogenicity To DTP-IPV four combined vaccine (acellular pertussis/diphtheria/tetanus/inactivated polio (Sabin strain) combined vaccine; Quattrovac (trade-name) manufactured by The Chemo-Sero-Therapeutic Research Institute) or to a mixture of acellular pertussis/diphtheria/tetanus combined vaccine (manufactured by The Chemo-Sero-Therapeutic Research Institute) and inactivated poliovirus (IPV; Salk strain) was added PRP conjugate to prepare five combined vaccines.

Figure 4:
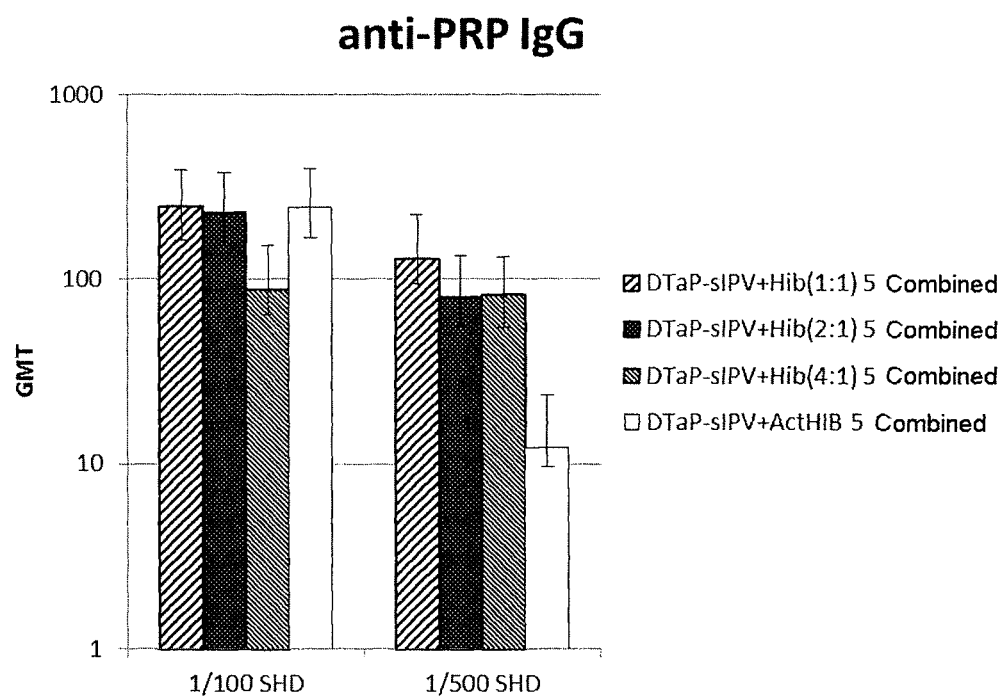

SD rats (female, 5 weeks old; each group consists of 5 animals) were subcutaneously inoculated at the back with 0.5 mL of Hib conjugate vaccine comprising as an antigen PRP conjugate (molecular weight of PRP: changing molecular weights such as Native, 155, 108, and 88 kDa, or with changing weight ratio of PRP and a carrier protein as prepared in Example 2). After four weeks, a second inoculation was performed. Two weeks after the second inoculation, blood was sampled and an antibody titer was measured with self-prepared ELISA. The results are shown in FIG. 4. Only one hundredth Single Human Dose (1/100 SHD) of the five combined vaccine in which PRP and a carrier protein was reacted at a weight ratio of 4:1 showed a little lower anti-PRP antibody titer but the other five combined vaccines showed anti-PRP antibody titer equivalent to or more than that of the five combined vaccine using the known Hib conjugate vaccine (ActHIB (trade-name) manufactured by Sanofi Pasteur). The reaction condition of a weight ratio of 4:1 showed a higher antibody titer than ActHIB (trade-name) at 1/500 SHD.

Figure 5:
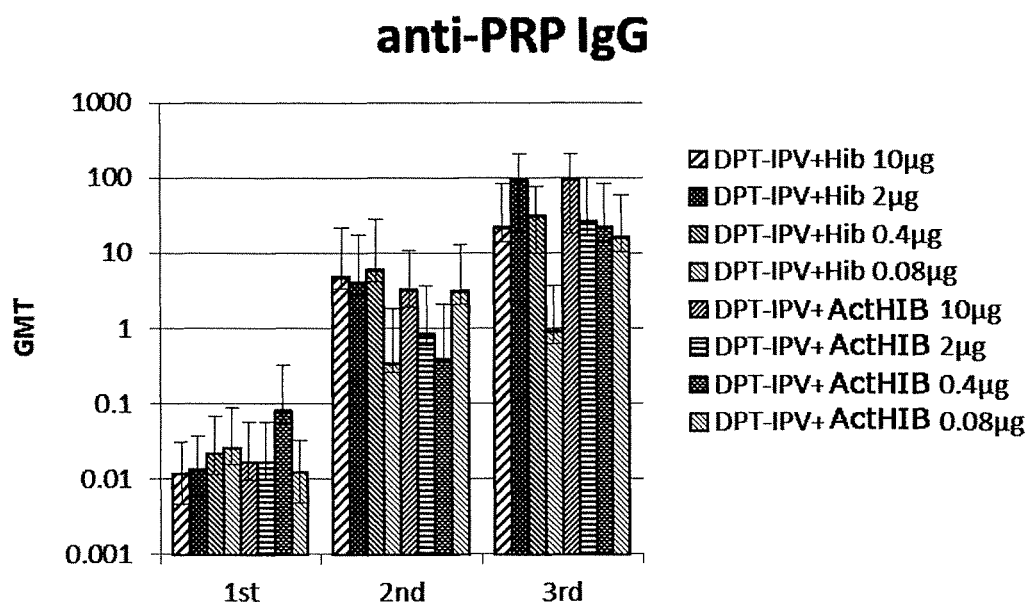

Immunogenicity of the five combined vaccines as prepared was investigated. Rats (Wister, female, 8 weeks old; each group consists of 10 animals) were subcutaneously administered at the back three times every three weeks. Three weeks after the inoculation, blood was sampled and an antibody titer was measured with self-prepared ELISA. The results are shown in FIG. 5. In comparison with the five vaccine combined with the known Hib conjugate vaccine (ActHIB (trade-name) manufactured by Sanofi Pasteur) at changing doses, it was found that, after the third inoculation, an antibody titer was highest at 10 μg of the known Hib conjugate vaccine whereas it was highest at 2 μg of Hib conjugate vaccine of the present invention, suggesting that equivalent immunogenicity may be obtained with a lesser amount of the Hib conjugate vaccine of the present invention.

Example 7

Evaluation of Stability of PRP Conjugate Drug Substance

Hib drug substances with changing concentration and pH were heated at 37° C. for 1 week to evaluate stability. The results are shown in Table 2. As a storage condition of drug substance, a higher concentration proved more stable. Under the condition of a higher concentration, stability was higher at pH 6.0 than at pH 6.8.

TABLE 2

| Samples | Buffer | PRP conc. [mg/mL] | Free PRP (%) 37° C. 0 w | Free PRP (%) 37° C. 1 w | Increased amount (1 w − 0 w) |
|---|---|---|---|---|---|
| Hib A | 10 mM PBS (pH 6.8) | 0.5 | 10.8 | 21.9 | 11.1 |
| | 20 mM PBS (pH 6.0) | 0.5 | 10.8 | 19.5 | 8.7 |
| | 10 mM PBS (pH 6.8) | 1 | 10.8 | 19.3 | 8.5 |
| | 20 mM PBS (pH 6.0) | 1 | 10.8 | 16.5 | 5.7 |
| Hib B | 10 mM PBS (pH 6.8) | 0.5 | 6.9 | 17.9 | 11.0 |
| | 20 mM PBS (pH 6.0) | 0.5 | 6.9 | 17.3 | 10.4 |
| | 10 mM PBS (pH 6.8) | 1 | 6.9 | 15.3 | 8.4 |
| | 20 mM PBS (pH 6.0) | 1 | 6.9 | 13.2 | 6.3 |

Example 8

Evaluation of Effect of pH on Stability of Mix Vaccine Comprising PRP Conjugate A buffer was added to combined vaccines so as to bring their pH to 5.0, 5.4, 5.7 and 6.0. Samples under consideration were heated at 37° C. for 4 weeks and free PRPs were measured. The results are shown in Table 3. The better results were obtained with the combined vaccines at pH of 6.0, 5.7, and 5.4 whereas the combined vaccines at pH 5.0 showed instability. Effect on immunogenicity of antigens other than Hib contained in the combined vaccines was also investigated but no effect of pH was shown.

TABLE 3

| Samples | Phosphate conc. | pH | 37° C., 4 w mean value (%) | 4° C., 4 w mean value (%) | Difference (%) |
|---|---|---|---|---|---|
| DTP-IPV (Sabine)-Hib | 20 mM | 5.0 | 38.0 | 7.46 | 30.5 |
| | | 5.4 | 24.7 | 8 | 16.7 |
| | | 5.7 | 21.0 | 8.3 | 12.70 |
| | | 6.0 | 22.8 | 8.59 | 14.2 |
| | 50 mM | 5.0 | 30.8 | 7.9 | 22.9 |
| | | 5.4 | 23.5 | 8.2 | 15.3 |
| | | 5.7 | 21.8 | 7.7 | 14.1 |
| | | 6.0 | 23.9 | 8.3 | 15.60 |
| DTP-IPV (Salk)-Hib | 20 mM | 6.0 | 27.5 | 18.8 | 8.70 |
| | | 7.0 | 45.9 | 25.1 | 20.8 |

Figure 6:
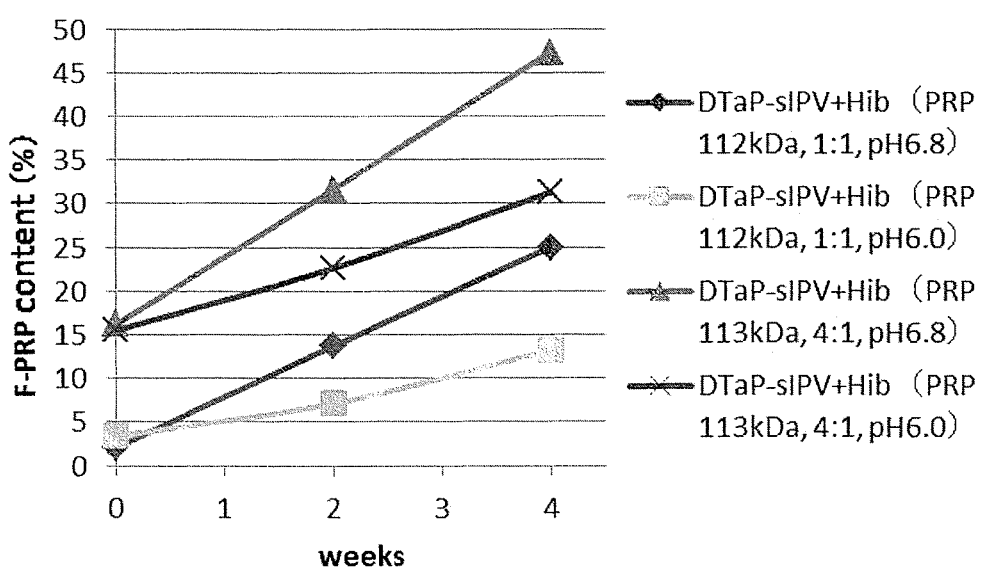
Figure 7:
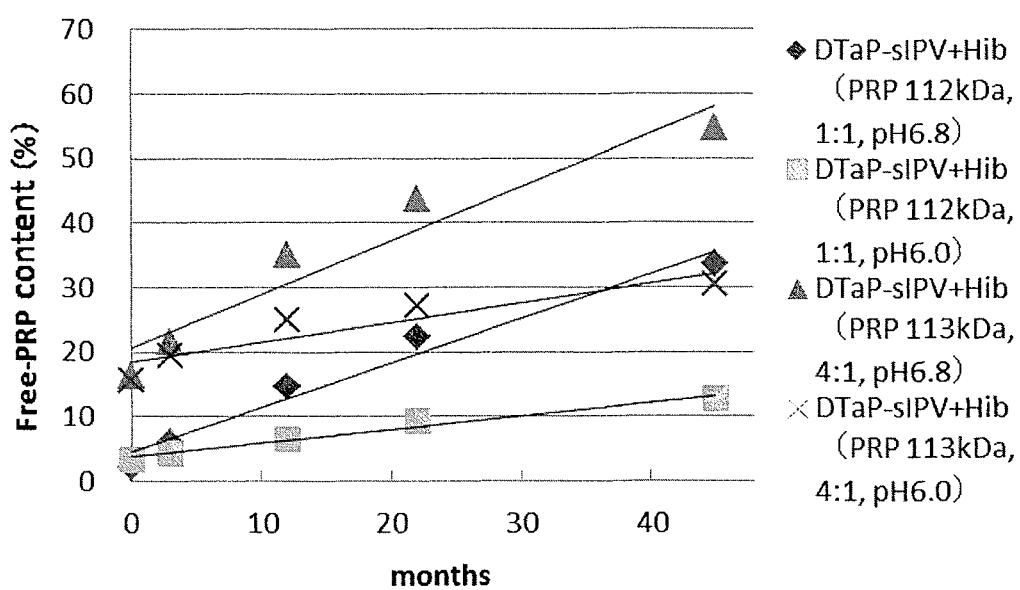

In case that the combined vaccines at pH of 6.0 or 6.8 were heated at 37° C. for 4 weeks, the vaccines were stored at 10° C. for 45 months and free PRPs were measured. The results are shown in FIGS. 6 and 7. The Hib conjugate combined vaccine comprising as an antigen PRP conjugate prepared in accordance with one embodiment of the present invention showed higher stability at pH 6.0 than at pH 6.8. Heating at 37° C. for 2 weeks showed free PRP values nearly equivalent to those obtained when heating at 10° C. for 12 months. Heating at 37° C. for 4 weeks showed free PRP values nearly equivalent to those obtained when heating at 10° C. for 45 months. As apparent from FIGS. 6 and 7, similar tendency was confirmed for both heating at 37° C. and storage at 10° C.

INDUSTRIAL APPLICABILITY

The method for preparation according to the present invention may be used for production of a Hib conjugate vaccine and for production of a combined vaccine comprising the Hib conjugate vaccine.

The invention claimed is:

1. A method for preparing a polyribosylribitol phosphate (PRP) conjugate via a coupling reaction of PRP and a carrier protein wherein the method is characterized by that the release of PRPs after preparing the PRP conjugate is suppressed by using PRP with a lowered molecular weight than native PRP, wherein the PRP conjugate is stored in a solution of pH 5.4 to 6.3 after preparation of the PRP conjugate.

2. The method of claim 1 wherein a released amount of PRPs in a stress test in a solution at pH 5.4 to 6.3 at 37° C. for 4 weeks is less than 50%.

3. The method of claim 1 wherein PRP with a lowered molecular weight is obtained by physical fracture.

4. The method of claim 1 wherein PRP with a lowered molecular weight is obtained by hydrolysis with an acid or an alkali.

5. The method of claim 1 wherein PRP with a lowered molecular weight has a molecular weight of 80 to 150 kDa.

6. The method of claim 1 wherein PRP and the carrier protein is subject to the coupling reaction for preparing the PRP conjugate at a weight ratio of from 2:1 to 4.1.

7. The method of claim 6 wherein PRP and the carrier protein are subject to the coupling reaction at a weight ratio of 4:1.

8. The method of claim 1 wherein the method comprises a step of activating PRP with a lowered molecular weight using 1-cyano-4-(dimethylamino) pyridinium tetrafluoroborate (CDAP) before the coupling reaction for preparing the PRP conjugate.

9. The method of claim 1 wherein the carrier protein is tetanus toxoid.

10. The method of claim 9 wherein a purity of tetanus toxoid is 2,500 to 3,500 LF/mg PN.

11. The method of claim 10 wherein a purity of tetanus toxoid is 2,900 to 3,300 LF/mg PN.

12. A method for producing a *Haemophilus influenzae* type b (Hib) conjugate vaccine comprising the method as set forth in claim 1.

* * * * *